United States Patent
Ancona

(10) Patent No.: US 6,612,309 B1
(45) Date of Patent: Sep. 2, 2003

(54) VENTILATOR TUBE RETENTION STRAP FOR USE WITH ENDOTRACHEAL OR TRACHEOSTOMY TUBE

(75) Inventor: Cindy Lou Ancona, 7103 Eva Dr., Rockford, MI (US) 49341

(73) Assignee: Cindy Lou Ancona, Rockford, MI (US)

( * ) Notice: Subject to any disclaimer, the term of this patent is extended or adjusted under 35 U.S.C. 154(b) by 0 days.

(21) Appl. No.: 09/987,800

(22) Filed: Nov. 16, 2001

Related U.S. Application Data

(60) Provisional application No. 60/294,992, filed on Jun. 4, 2001.

(51) Int. Cl.[7] .............................................. A61M 16/00
(52) U.S. Cl. .............................. 128/207.17; 128/207.14
(58) Field of Search ....................... 128/207.14, 207.15, 128/207.17, 207.29, 912, DIG. 26, 200.26; 2/137, 181.2, 59, 460

(56) References Cited

U.S. PATENT DOCUMENTS

| | | | | |
|---|---|---|---|---|
| 3,987,798 A | * | 10/1976 | McGinnis | 128/207.17 |
| 4,266,511 A | * | 5/1981 | Muench | 119/858 |
| 4,331,143 A | * | 5/1982 | Foster | 128/207.17 |
| 4,641,646 A | * | 2/1987 | Schultz et al. | 128/207.14 |
| 5,009,227 A | * | 4/1991 | Nieuwstad | 128/207.17 |
| 5,010,884 A | * | 4/1991 | Van Derdoes et al. | 128/207.17 |
| 5,101,822 A | * | 4/1992 | Kimmel | 128/207.14 |
| 5,205,832 A | * | 4/1993 | Tuman | 604/179 |
| 5,233,979 A | * | 8/1993 | Strickland | 128/207.14 |
| 5,282,463 A | * | 2/1994 | Hammersley | 128/207.15 |
| 5,357,952 A | * | 10/1994 | Schuster et al. | 128/207.17 |
| 5,368,023 A | * | 11/1994 | Wolf | 128/207.17 |
| 5,437,273 A | * | 8/1995 | Bates et al. | 128/207.17 |
| 5,456,274 A | * | 10/1995 | Selbee et al. | 132/275 |
| 5,529,062 A | * | 6/1996 | Byrd | 128/207.17 |
| 5,782,236 A | * | 7/1998 | Ess | 128/207.17 |
| 5,839,437 A | * | 11/1998 | Briggs, III | 128/207.17 |
| 6,047,699 A | * | 4/2000 | Ryatt et al. | 128/207.17 |
| 6,105,573 A | * | 8/2000 | Delaplane et al. | 128/200.26 |
| 6,336,457 B1 | * | 1/2002 | Hudson et al. | 128/207.17 |
| 6,394,092 B1 | * | 5/2002 | Barrett et al. | 128/207.17 |
| 6,412,117 B1 | * | 7/2002 | Holmes et al. | 2/137 |

\* cited by examiner

*Primary Examiner*—Weilun Lo
*Assistant Examiner*—Teena Mitchell
(74) *Attorney, Agent, or Firm*—Schuster et al.

(57) ABSTRACT

A ventilator tube retention strap for releasably securing a medical ventilator tube to a tracheotomy tube apparatus. The ventilator tube retention strap is comprised of an elongate, flexible strap and a sheath or cover, which substantially encloses the elongate, flexible strap. The flexible strap is defined by first and second opposing ends, each of which is configured as a loop enclosing an aperture. The ventilator tube retention strap is wrapped around the neck of a patient, and the loops are coaligned to receive in frictional engagement the medical ventilator tube, which is then attached to an external tube of the tracheotomy tube apparatus and maintained thereon by the ventilator tube retention strap.

4 Claims, 2 Drawing Sheets

VENTILATOR TUBE RETENTION STRAP FOR USE WITH ENDOTRACHEAL OR TRACHEOSTOMY TUBE

This application claims the benefit of provisional application 60/294,992 filed Jun. 4, 2001.

BACKGROUND OF THE INVENTION

This version of the invention is concerned with the field of medical ventilator and endotracheal or tracheostomy tubes. More specifically, this version of the invention is concerned with retention devices or straps that are fastened to or secured around the neck of a patient in order to support a ventilator tube in attachment to or communication with an endotracheal or tracheostomy tube already inserted through a stoma in the patient's throat and into the trachea or windpipe.

Patients with certain medical conditions require insertion of an endotracheal or tracheostomy tube into their necks as part of the tracheotomy procedure to assist in breathing before, during, and after treatment. A tracheostomy tube apparatus is employed and is typically comprised of a flexible band or flange, which supports external and internal tracheostomy tubes, and a resilient collar. The tracheostomy tube apparatus is positioned around the neck of a patient and the internal tube, which communicates with the external tube, is inserted into the stoma. The collar is secured at opposing ends to the band or flange and is wrapped around the neck or adjacent portions of the head of a patient. A ventilator tube and adjoining tubular apparatus is releasably attached at a first end to the external tube of the tracheostomy tube apparatus at a second end to a mechanical breathing device. The ventilator tube remains attached to the external tube of the tracheostomy tube apparatus until the patient requires suctioning. Inevitably the ventilator tube becomes separated from the external tube of the tracheostomy tube apparatus while, for instance, the patient is sleeping or is engaged in activities that are normally encountered during a hospital stay.

When suctioning is necessary, the ventilator tube and adjoining tubular apparatus are separated from the tracheostomy tube apparatus and are situated at a nearby location. Depending upon the duration and nature of the procedure, it is not uncommon for the ventilator tube and adjoining tubular apparatus to become dislocated or otherwise repositioned at a location at some distance from the original location. Various means and devices have been improvised to secure the ventilator tube to the tracheostomy tube apparatus, such as rubber bands and cotton tape. Rubber bands are less than an effective means, as it is difficult if not impossible to find a suitable location on the ventilator tube or the tracheostomy tube apparatus to attach the rubber bands. Furthermore, rubber bands may break and sting the patient or press uncomfortably against the neck. Strips of cotton tape are usually tied at one end to the ventilator tube and at a second end to the tracheostomy tube apparatus. Inevitably, the strips of cotton tape are tied with uneven force, causing discomfort for the patient. Furthermore, the cotton tape is not resilient and may constrict against the neck if tied too tightly or if the patient's neck expands.

What is needed then to ensure that a ventilator tube remains attached to a tracheostomy tube apparatus or maintained at a proximate location during separation or disconnection of said tubes is the provision of a ventilator tube retention strap. Such a device would be fabricated as a flexible strap with protective covering and two looped ends, each of which encloses an aperture. The device would be wrapped around the neck of a patient so that the apertures of the looped ends would align, thereby allowing the looped ends to secure a ventilator tube to an adjacent tracheostomy tube apparatus as the looped ends of the flexible strap simultaneously pull in opposing direction and toward the tracheostomy tube apparatus.

SUMMARY OF THE INVENTION

The present version of the invention, which will be described in greater detail hereinafter, relates to the field of medical ventilator and endotracheal tubes. More specifically, this version of the invention is concerned with retention straps that are fastened to or secured around the neck of a patient in order to support a ventilator tube in attachment to or communication with an endotracheal or tracheostomy tube already inserted through a stoma in the patient's throat and into the trachea or windpipe. My version of the invention overcomes all of the shortcomings listed previously, in addition to novel aspects that will be described in detail hereinafter.

Described briefly, according to a typical embodiment, the invention presents a ventilator tube retention strap that consists of a flexible, resilient inner strap and a resilient outer cover, sheath, or sleeve that substantially encloses the inner strap. Each end of the inner strap is configured as a loop enclosing an aperture. During use, the unattached end of a ventilator tube is inserted into the first loop of the retention strap. The inner strap and outer cover are then wrapped around the neck of a patient until it is possible to fit the second loop over the unattached end of the ventilator tube at which time the ventilator tube can be connected to the tracheostomy tube apparatus. As the inner strap and outer strap are resilient, they will pull or urge the ventilator tube inward toward the tracheostomy tube apparatus, ensuring that the ventilator tube maintains secure contact thereon. During suctioning, the ventilator tube, while secured to the retention strap, can be easily disconnected from the tracheostomy tube and moved to either side of the neck of the patient and reattached to the tracheostomy tube when the procedure is completed.

My invention, therefore, resides not in any one of these features per se, but rather in the particular combination of all of them herein disclosed. It is distinguished from the prior art in this particular combination of all of its structures for the functions specified. In order that the detailed description of the invention may be better understood and that the present contribution to the art can be more fully appreciated, additional features of the invention will be described hereinafter. It should be appreciated by those skilled in the art that the conception and the disclosed specific methods and structures may be readily utilized as a basis for modifying or designing other structures for carrying out the same purposes of the present invention and that such equivalent methods and structures do not depart from the spirit and scope of the invention.

OBJECTS OF THE INVENTION

Accordingly, it is an object of my version of the invention to provide a low-cost, easy-to-manufacture, and easy-to-market ventilator tube retention strap.

A further object of my version of the invention is to provide an easy-to-use and versatile ventilator tube retention strap.

A significant object of the invention is to provide a ventilator tube retention strap that is comprised of an inner strap of flexible, resilient material with looped ends, each looped end enclosing an aperture, and a resilient outer cover, sheath, or sleeve substantially enclosing the inner strap.

A final but very significant object of the invention is to provide a ventilator tube retention strap that is simplified in design and construction so as to permit quick and easy attachment to a ventilator tube and during said attachment makes possible a secure connection of said ventilator tube to a tracheostomy tube apparatus.

Other objects and advantages of the present invention will become apparent from the following descriptions, taken in connection with the accompanying drawings, wherein, by way of illustration and example, various embodiments of the present invention are disclosed.

The drawings constitute a part of this specification and include exemplary embodiments to the invention, which may be embodied in various forms. It is to be understood that in some instances various aspects of the invention may be shown exaggerated or enlarged to facilitate an understanding of the invention.

DRAWING REFERENCE NUMERALS

10 Tracheotomy Tube Apparatus
12 External Tube
14 Annular Flange
16 Internal Tube
18 Flange
20 Slot
22 Slot
24 Collar
26 First End of Collar
28 Second End of Collar
30 First Strap
32 Second Strap
34 Ventilator Tube
36 Cylindrical Fitting
38 Ventilator Tube Retention Strap
40 Inner Strap
42 Strap Cover
44 First End of Strap Cover
46 Second End of Strap Cover
48 First End of Inner strap
50 Second End of Inner strap
52 First Loop
54 Second Loop
56 Aperture

DETAILED DESCRIPTION OF THE PREFERRED EMBODIMENT

A detailed description of the preferred embodiment is provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
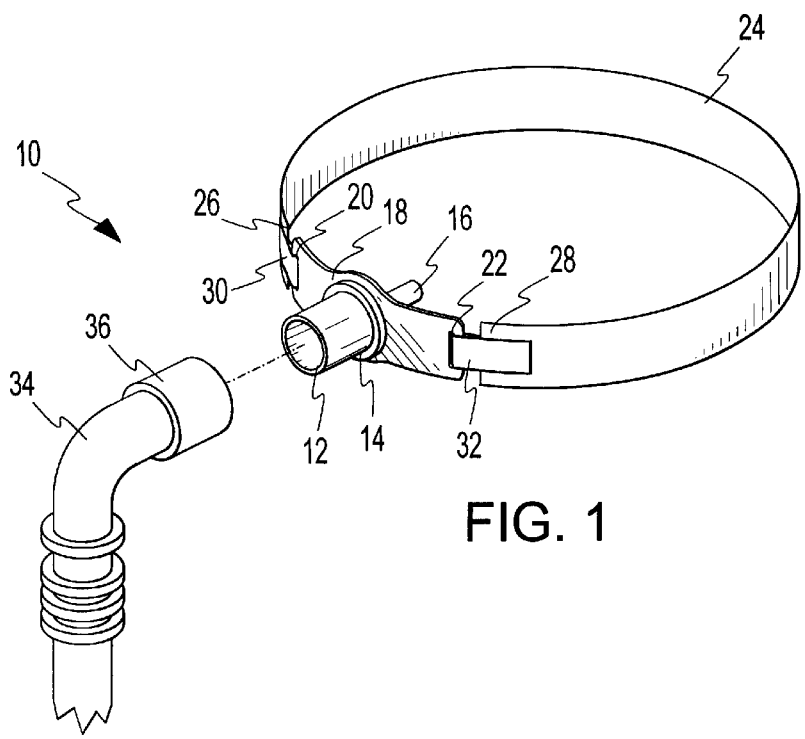
FIG. 1 is a perspective view of a tracheostomy tube apparatus, comprised of a tracheostomy tube, flange and collar, and a ventilator tube aligned for releasable attachment to the tracheostomy tube thereof.

Referring now to the drawings and, in particular, to FIG. 1 wherein there is illustrated a or endotracheal tube or tracheotomy tube apparatus 10 designed for releasable attachment to the neck of a patient after a tracheotomy has been performed. The apparatus 10, which is representative of current tracheotomy tube design and art, is comprised of a hollow external tube 12 with annular flange 14, internal tube 16, and belt-like flange 18. The belt-like flange 18 supports the tubes 12, 16 against the patient's neck at proper alignment thereto. The external tube 12 communicates with the internal tube 16, said internal tube 16 designed for insertion through a stoma in the patient's throat and into the trachea or windpipe to deliver slightly pressurized air to aid in respiration. First 20 and second 22 slots are located at opposing ends of the belt-like flange 18. A flexible collar 24 with first 26 and second 28 opposing ends is wrapped or coiled as displayed to encircle a patient's neck and maintain the flange 18 against the patient's neck. Straps 30, 32 are inserted through and looped around slots 20, 22 of the flange 18 and are releasably attached to first 26 and second 28 ends of the collar 24. The straps 30, 32 are releasably attached to one or both sides of the ends 26, 28 of the collar 24 using various means, such as hook and loop textile, commonly known by the trade name of VELCRO, or the like. A ventilator tube 34 having a cylindrical fitting 36 located at one end thereof is aligned for releasable attachment to the external tube 12 of the tracheotomy tube apparatus 10.

Figure 2:
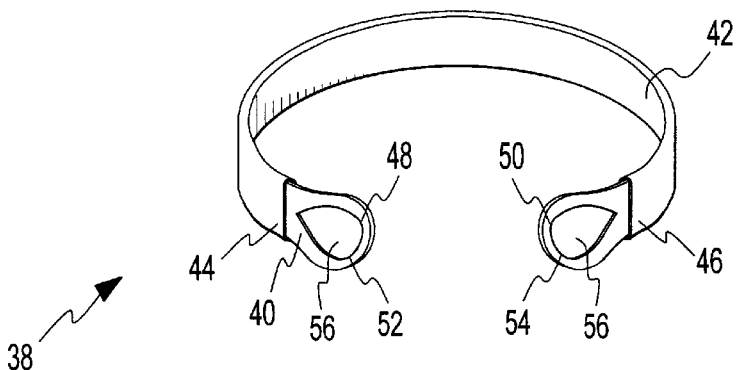
FIG. 2 is a perspective view of a ventilator tube retention strap in accordance with the present version of the invention.
Figure 3:
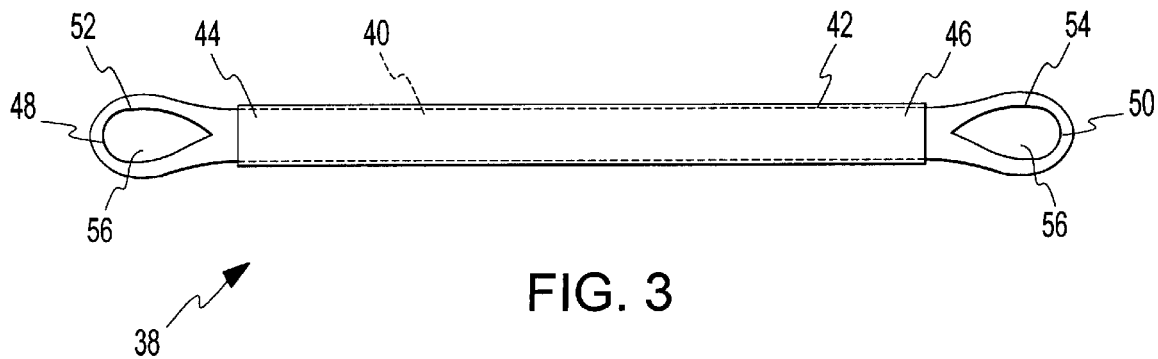
FIG. 3 is a side view of a ventilator tube retention strap illustrated in an unrolled or unfurled configuration.

Referring now in particular to FIG. 2 and FIG. 3 wherein there are illustrated a typical embodiment of the ventilator tube retention strap 38. The present version of the invention 38 is comprised of an inner strap 40 and an outer strap cover 42, sleeve, or sheath, said strap cover 42 having opposing first 44 and second 46 ends. The strap cover 42 can be attached directly to the inner strap 40 or disposed over the strap 40 in sliding engagement. The inner strap 40 and strap cover 42 are fabricated of various textile materials and are configured into a narrow, elongate shape. The textile materials can incorporate a weave pattern or elastic or resilient filaments, such as rubber strands, that permit the inner strap 40 and strap cover 42 to assume their original length after being stretched repeatedly. The strap 40 is defined by opposing first 48 and second 50 ends, which are configured into first 52 and second 54 loops, respectively. The loops 52, 54 encircle respective oval-shaped apertures 56, said loops 52, 54 able to expand and constrict to receive and fasten onto objects disposed within said apertures 56.

Figure 4:
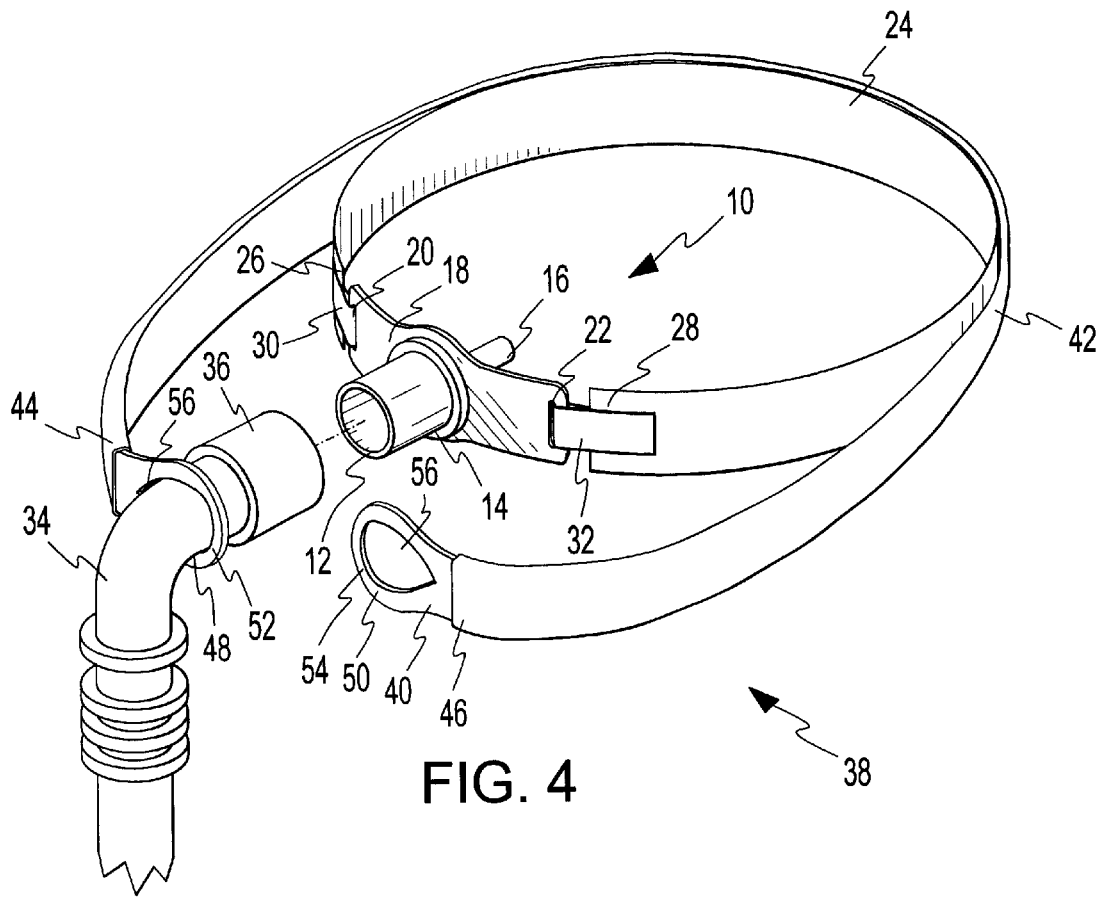
FIG. 4 is a perspective view of the ventilator tube retention strap partially wrapped around the collar of a tracheostomy tube apparatus with a first end of said strap releasably affixed onto a ventilator tube, which is aligned for attachment to a tracheostomy tube, and a second, unattached end of said ventilator tube retention strap disposed adjacent to the ventilator tube before attachment thereon.

Referring now to FIG. 4, the tracheotomy tube apparatus 10 is configured as required for releasable attachment to the neck of a patient in order to provide slightly pressurized air into the trachea or windpipe for assistance in respiration. The flange 18 with external 12 and internal 16 tubes is releasably attached by straps 30, 32 to cooperating ends 26, 28 of the collar 24. The ventilator tube retention strap 38 is secured to the ventilator tube 34 before said ventilator tube 34 is affixed to the external tube 12 using the following procedure. With the tracheotomy tube apparatus 10 already wrapped around a patient's neck, the cylindrical fitting 36 of the ventilator tube 34 is inserted into the aperture 56 of a loop 52 of the retention strap 38 and then the inner strap 12 and strap cover 14 are stretched and wrapped around the neck of the patient until it is possible to position the remaining loop 54 at a location adjacent to the unattached end of the cylindrical fitting 36. The remaining loop 54 is then secured over the cylindrical fitting 36, ensuring that said fitting 36 is received completely within the aperture 56 of the loop 54.

Figure 5:
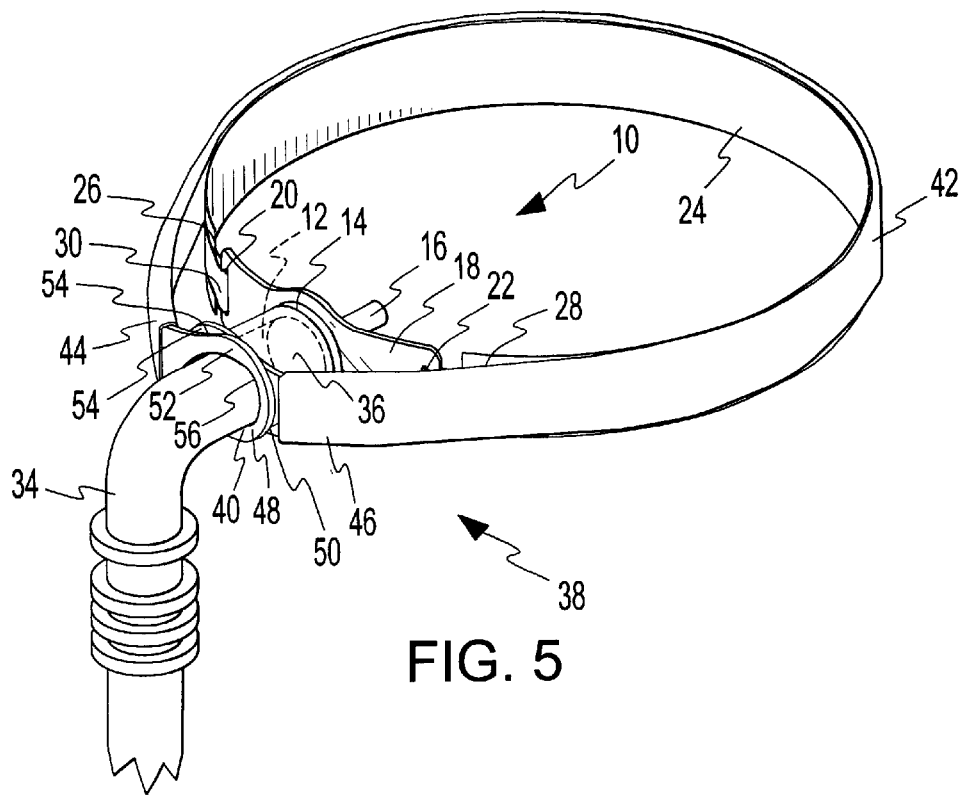
FIG. 5 is a perspective view of the ventilator tube retention strap wrapped around the collar of a tracheostomy tube apparatus and releasably affixed at opposing ends to a ventilator tube already attached to a tracheostomy tube in order to prevent said ventilator tube from becoming detached from said tracheostomy tube.

Once the cylindrical fitting 36 of the ventilator tube 34 is received within the apertures 56 of both loops 52, 54 and properly positioned with respect to the external tube 12 of the tracheotomy tube apparatus 10 and the neck of the patient, the inner strap 40, strap cover 42, and loops 52, 54 can be released. The elastic material of the inner strap 40 will urge in opposing directions against the ventilator tube 34 adjacent to the cylindrical fitting 36 and constrict gently around the neck of the patient, thereby pulling the ventilator tube 34 toward the tracheotomy tube apparatus 10, as illustrated in FIG. 5. The ventilator tube 34 is thus releasably affixed to the external tube 12 of the tracheotomy tube apparatus 10 in frictional engagement, whereby the cylindrical fitting 36 receives said external tube 12 and urges toward the flange 18 until the unattached end of the fitting 36 makes contact with the annular flange 14.

If necessary, the ventilator tube 34 can be easily disconnected from the tracheotomy tube apparatus 10 to allow suctioning by detaching the cylindrical fitting 36 of the ventilator tube 34 from the external tube 12 of the tracheotomy tube apparatus 10, ensuring that said cylindrical fitting 36 of said tube 34 remains within the loops 52, 54 of the retention strap 38, and positioning the ventilator tube 34 off to one side of the neck of the patient away from the tracheotomy tube apparatus 10. Once suctioning has been completed, the ventilator tube 34 can be reattached to the external tube 12 of the tracheotomy tube apparatus 10.

While this version of the invention has been illustrated and described in detail in the drawings and foregoing description, the same is to be considered as illustrative and not restrictive in character, it being understood that only the preferred embodiment has been shown and described and that all changes and modifications that come within the spirit of the version of the invention are desired to be protected.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

CONCLUSION AND SCOPE OF INVENTION

From the foregoing, it will be understood by persons skilled in the art that an improved ventilator tube retentions strap has been provided. The invention is relatively simple and easy to manufacture, yet affords a variety of uses. While my description contains many specificities, these should not be construed as limitations on the scope of the version of the invention, but rather as an exemplification of the preferred embodiments thereof. The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention. Although this invention has been described in its preferred forms with a certain degree of particularity, it is understood that the present disclosure of the preferred form has been made only by way of example and numerous changes in the details of construction and combination and arrangement of parts may be resorted to without departing from the spirit and scope of the invention.

While the invention has been described in connection with the preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A ventilator tube retention strap (38) for releasable securing a medical ventilator tube having a cylindrical fitting at one end thereof to a tracheotomy tube apparatus; said tube tracheotomy apparatus comprised of a collar (24) adapter to encircle the neck of a patient, external tube (12) and internal tube (16) disposed within a flange having first and second opposed end sections (18), said section each having a slot (20, 22) and straps (30, 32) inserted through the slots and wrapped around adjacent ends of said flange for releasable attachment to said collar (24); the ventilator tube retention strap comprising:

(a) an elongated, resilient inner strap (40) having first (48) and second (50) opposed ends, each end configured into fastening means (48, 50, 52, 54, 56); said fastening means comprising a first (52) and second loop (54), each loop having an oval aperture (56), in which the apertures (56) of the loops (52, 54) are adapted to receive an unattached end of a medical ventilator tube (34) and permit said loops (52, 54) to retain in frictional engagement an end of a medical ventilator tube (34), when said inner strap (40) is wrapped around the collar of a tracheotomy tube apparatus, thus releasable securing said medical ventilator tube (34) to said tracheotomy tube apparatus; and (b) an elongated, resilient strap cover (42) disposed over said inner strap (40).

2. A ventilator tube retention strap as recited in claim 1, in which the elongate, inner strap is comprised of textile material having a weave pattern interwoven with elastic or resilient material, such as rubber, or the like.

3. A ventilator tube retention strap as recited in claim 1, in which the strap cover is comprised is comprised of first and second opposing ends.

4. A ventilator tube retention strap as recited in claim 3, in which the strap cover substantially encloses the elongate, inner strap between first and second opposing ends of said strap cover, allowing the looped ends of the elongate, inner strap to remain exposed.

* * * * *